US010288633B2

(12) United States Patent
Luoma et al.

(10) Patent No.: US 10,288,633 B2
(45) Date of Patent: May 14, 2019

(54) REACTION VESSEL MOVING MEMBER FOR MOVING REACTION VESSELS FROM A PROCESSING TRACK TO A ROTATING DEVICE IN A DIAGNOSTIC ANALYZER

(71) Applicant: Abbott Laboratories, Abbott Park, IL (US)

(72) Inventors: Robert Luoma, Colleyville, TX (US); Ryan Patrick Johnson, Bedford, TX (US)

(73) Assignee: ABBOTT LABORATORIES, Abbott Park, IL (US)

(*) Notice: Subject to any disclaimer, the term of this patent is extended or adjusted under 35 U.S.C. 154(b) by 86 days.

(21) Appl. No.: 15/193,786

(22) Filed: Jun. 27, 2016

(65) Prior Publication Data

US 2016/0377641 A1    Dec. 29, 2016

Related U.S. Application Data

(60) Provisional application No. 62/185,546, filed on Jun. 26, 2015.

(51) Int. Cl.
*G01N 21/00* (2006.01)
*G01N 15/06* (2006.01)
(Continued)

(52) U.S. Cl.
CPC ............ *G01N 35/04* (2013.01); *G01N 35/021* (2013.01); *G01N 35/025* (2013.01); *G01N 2035/0408* (2013.01); *G01N 2035/0443* (2013.01)

(58) Field of Classification Search
CPC ........ G01N 21/00; G01N 15/06; G01N 33/00; G01N 33/48

USPC ..... 422/50, 68.1, 82.05, 554, 560, 561, 565, 422/566, 63, 64, 65, 66, 129; 436/43, 436/164, 165
See application file for complete search history.

(56) References Cited

U.S. PATENT DOCUMENTS

| 3,909,203 A | 9/1975 | Young et al. |
| 4,276,051 A | 6/1981 | Ginsberg et al. |

(Continued)

FOREIGN PATENT DOCUMENTS

| CN | 1039901 A | 2/1990 |
| CN | 1305585 A | 7/2001 |

(Continued)

OTHER PUBLICATIONS

International Search Report and Written Opinion from corresponding International Application PCT/US16/39559 dated Sep. 15, 2016, 11 pages.

(Continued)

*Primary Examiner* — Brian J. Sines
(74) *Attorney, Agent, or Firm* — Klintworth & Rozenblat IP LLP

(57) ABSTRACT

A diagnostic analyzer includes a rotating device, a first optical reader, and a second optical reader. The rotating device includes a first darkened compartment, a second darkened compartment, and an optical path along which the first darkened compartment and the second darkened compartment travel. The first optical reader is operable to read the first darkened compartment and the second optical reader is operable to read the second darkened compartment.

20 Claims, 13 Drawing Sheets

(51) Int. Cl.
  *G01N 33/00*  (2006.01)
  *G01N 33/48*  (2006.01)
  *G01N 35/04*  (2006.01)
  *G01N 35/02*  (2006.01)

(56) References Cited

U.S. PATENT DOCUMENTS

| | | |
|---|---|---|
| 4,411,518 A | 10/1983 | Meserol et al. |
| 4,609,017 A | 9/1986 | Coulter et al. |
| 4,609,291 A | 9/1986 | Takahashi |
| 4,683,120 A | 7/1987 | Meserol et al. |
| 4,753,775 A | 6/1988 | Ebersole et al. |
| 5,053,197 A | 10/1991 | Bowen |
| 5,077,013 A | 12/1991 | Guigan |
| 5,110,552 A | 5/1992 | Guigan |
| 5,128,105 A | 7/1992 | Berthold |
| 5,128,808 A | 7/1992 | Dosaka |
| 5,137,693 A | 8/1992 | Mawhirt |
| 5,139,744 A | 8/1992 | Kowalski |
| 5,141,871 A | 8/1992 | Kureshy |
| 5,158,748 A | 10/1992 | Obi |
| 5,158,895 A | 10/1992 | Ashiara |
| 5,167,926 A | 12/1992 | Kimura |
| 5,173,741 A | 12/1992 | Wakatake |
| 5,178,834 A | 1/1993 | Kagayama et al. |
| 5,192,506 A | 3/1993 | Kureshy |
| 5,228,988 A | 7/1993 | Sanford et al. |
| 5,240,678 A | 8/1993 | Rochester |
| 5,246,665 A | 9/1993 | Tyranski |
| 5,294,404 A | 3/1994 | Grandone |
| 5,306,510 A | 4/1994 | Meltzer |
| 5,320,808 A | 6/1994 | Holen et al. |
| 5,324,481 A | 6/1994 | Dunn et al. |
| 5,340,544 A | 8/1994 | Nishikawa |
| 5,366,697 A | 11/1994 | Tomasso |
| 5,374,395 A | 12/1994 | Robinson |
| 5,380,666 A | 1/1995 | Wuerschum |
| 5,411,065 A | 5/1995 | Meador |
| 5,424,036 A | 6/1995 | Ushikubo |
| 5,443,791 A | 8/1995 | Cathcart |
| 5,455,006 A | 10/1995 | Aota |
| 5,462,715 A | 10/1995 | Koch et al. |
| 5,482,861 A | 1/1996 | Clark |
| 5,501,838 A | 3/1996 | Ootani |
| 5,578,268 A | 11/1996 | Champseix et al. |
| 5,582,796 A | 12/1996 | Carey |
| 5,585,068 A | 12/1996 | Panetz |
| 5,605,665 A | 2/1997 | Clark |
| 5,610,069 A | 3/1997 | Clark |
| 5,623,415 A | 4/1997 | O'Bryan |
| 5,635,364 A | 6/1997 | Clark |
| 5,637,275 A | 6/1997 | Carey |
| 5,645,800 A | 7/1997 | Masterson |
| 5,658,532 A | 8/1997 | Kurosaki et al. |
| 5,663,545 A | 9/1997 | Marquiss |
| 5,670,375 A | 9/1997 | Seaton |
| 5,714,127 A | 2/1998 | Dewitt |
| 5,720,377 A | 2/1998 | Lapeus |
| 5,730,697 A | 3/1998 | Auchinleck |
| 5,735,387 A | 4/1998 | Polaniec |
| 5,736,102 A | 4/1998 | Seaton |
| 5,741,708 A | 4/1998 | Carey |
| 5,762,873 A | 6/1998 | Fanning |
| 5,762,874 A | 6/1998 | Seaton |
| 5,762,878 A | 6/1998 | Clark |
| 5,798,084 A | 8/1998 | Seaton |
| 5,798,085 A | 8/1998 | Seaton |
| 5,849,247 A | 12/1998 | Uzan et al. |
| 5,855,847 A | 1/1999 | Oonuma |
| 5,856,193 A | 1/1999 | Fanning |
| 5,895,628 A | 4/1999 | Heid et al. |
| 5,897,835 A | 4/1999 | Seaton |
| 5,965,090 A | 10/1999 | Fanning |
| 5,972,721 A | 10/1999 | Bruno |
| 6,006,800 A | 12/1999 | Nakano |
| 6,086,824 A | 7/2000 | Fanning |
| 6,098,819 A | 8/2000 | Hamburg |
| 6,111,930 A | 8/2000 | Schipper |
| 6,190,617 B1 | 2/2001 | Clark |
| 6,207,031 B1 | 3/2001 | Adourian |
| 6,325,114 B1 | 12/2001 | Bevirt |
| 6,358,470 B1 | 3/2002 | Higuchi |
| 6,358,471 B1 | 3/2002 | Ishihara |
| 6,372,185 B1 | 4/2002 | Shumate |
| 6,432,365 B1 | 8/2002 | Levin |
| 6,436,292 B1 | 8/2002 | Petro |
| 6,436,349 B1 | 8/2002 | Carey |
| 6,458,533 B1 | 10/2002 | Felder |
| 6,461,570 B2 | 10/2002 | Ishihara |
| 6,498,037 B1 | 12/2002 | Carey |
| 6,503,457 B1 | 1/2003 | Neeper |
| 6,566,143 B2 | 5/2003 | Hoyt |
| 6,656,428 B1 | 12/2003 | Clark et al. |
| 6,669,432 B2 | 12/2003 | Hudson |
| 6,678,577 B1 | 1/2004 | Stylli |
| 6,694,128 B1 | 2/2004 | Sorrells et al. |
| 6,767,511 B1 | 7/2004 | Rousseau |
| 6,780,648 B1 | 8/2004 | Sun |
| 6,803,239 B2 | 10/2004 | McLean |
| 6,808,935 B2 | 10/2004 | Levin |
| 6,919,044 B1 | 7/2005 | Shibata |
| 7,101,510 B2 | 9/2006 | Vann |
| 7,182,912 B2 | 2/2007 | Carey |
| 7,217,392 B2 | 5/2007 | Bogen |
| 7,335,338 B2 | 2/2008 | Schermer |
| 7,361,309 B2 | 4/2008 | Vann |
| 7,371,347 B2 | 5/2008 | Wulf |
| 7,435,383 B2 | 10/2008 | Tseung |
| 7,501,094 B2 | 3/2009 | Bysouth |
| 7,514,046 B2 | 4/2009 | Kechagia |
| 7,585,463 B2 | 9/2009 | Austin |
| 7,611,905 B2 | 11/2009 | Kunuki |
| 7,628,954 B2 | 12/2009 | Gomm |
| 7,670,553 B2 | 3/2010 | Babson |
| 7,681,466 B2 | 3/2010 | Miller |
| 7,713,708 B2 | 5/2010 | Roback |
| 7,718,435 B1 | 5/2010 | Bogen |
| 7,718,442 B2 | 5/2010 | Davis |
| 7,785,534 B2 | 8/2010 | Watari |
| 7,790,462 B2 | 9/2010 | Fournier |
| 7,815,866 B2 | 10/2010 | Safar |
| 7,854,891 B2 | 12/2010 | Yamamoto et al. |
| 7,854,892 B2 | 12/2010 | Veiner |
| 7,910,065 B2 | 3/2011 | Clark |
| 7,951,329 B2 | 5/2011 | Malyarov et al. |
| 7,959,875 B2 | 6/2011 | Zhou |
| 7,980,119 B2 | 7/2011 | Maeda et al. |
| 7,985,375 B2 | 7/2011 | Edens et al. |
| 7,987,736 B2 | 8/2011 | Rapaud |
| 7,998,751 B2 | 8/2011 | Evers et al. |
| 8,007,740 B2 | 8/2011 | Liu et al. |
| 8,008,066 B2 | 8/2011 | Lair |
| 8,021,611 B2 | 9/2011 | Roach |
| 8,038,942 B2 | 10/2011 | Ping |
| 8,057,756 B2 | 11/2011 | Londo et al. |
| 8,114,349 B2 | 2/2012 | Amirkhanian |
| 8,124,028 B2 | 2/2012 | Fulton |
| 8,142,739 B2 | 3/2012 | Tseung |
| 8,158,059 B2 | 4/2012 | Kennedy et al. |
| 8,182,745 B2 | 5/2012 | Chiba et al. |
| 8,182,761 B2 | 5/2012 | Nakagawa |
| 8,211,381 B2 | 7/2012 | Ricci et al. |
| 8,222,048 B2 | 7/2012 | Fritchie |
| 8,257,650 B2 | 9/2012 | Chow |
| 8,266,973 B2 | 9/2012 | Maeda et al. |
| 8,277,729 B2 | 10/2012 | Matsuo |
| 8,277,752 B2 | 10/2012 | Nakagawa |
| 8,278,108 B2 | 10/2012 | Wada et al. |
| 8,287,820 B2 | 10/2012 | Williams |
| 8,293,175 B2 | 10/2012 | Hotlund |
| 8,348,370 B2 | 1/2013 | Peters |
| 8,361,387 B2 | 1/2013 | Schacher et al. |
| 8,367,022 B2 | 2/2013 | Warhurst et al. |
| 8,372,355 B2 | 2/2013 | Zhou |

(56) References Cited

U.S. PATENT DOCUMENTS

| | | |
|---|---|---|
| 8,377,377 B2 | 2/2013 | Angros |
| 8,377,394 B2 | 2/2013 | Sakowski |
| 8,383,421 B2 | 2/2013 | Yanagida |
| 8,389,297 B2 | 3/2013 | Pamula |
| 8,486,335 B2 | 7/2013 | Angros |
| 8,492,155 B2 | 7/2013 | Bunce |
| 8,501,461 B2 | 8/2013 | Knight et al. |
| 8,535,624 B2 | 9/2013 | Luoma |
| 8,545,756 B2 | 10/2013 | Hotlund |
| 8,549,934 B2 | 10/2013 | Biksacky |
| 8,551,421 B2 | 10/2013 | Luchinger |
| 8,574,511 B2 | 11/2013 | Nakagawa |
| 8,585,987 B2 | 11/2013 | Tseung |
| 8,586,347 B2 | 11/2013 | Lochhead |
| 8,616,072 B2 | 12/2013 | Boeke et al. |
| 8,641,970 B2 | 2/2014 | Chung et al. |
| 8,663,991 B2 | 3/2014 | Reinhardt |
| 8,696,990 B2 | 4/2014 | Meller et al. |
| 8,703,070 B1 | 4/2014 | Parng et al. |
| 8,715,593 B2 | 5/2014 | Brewer et al. |
| 8,718,948 B2 | 5/2014 | Heinz et al. |
| 8,734,719 B2 | 5/2014 | Mototsu et al. |
| 8,747,745 B2 | 6/2014 | Kitaoka |
| 8,778,280 B2 | 7/2014 | Zhou |
| 8,804,114 B2 | 7/2014 | Ingber |
| 8,808,649 B2 | 8/2014 | Ingber et al. |
| 8,840,848 B2 | 9/2014 | Kraihanzel |
| 8,852,508 B2 | 10/2014 | Graf et al. |
| 8,883,509 B2 | 11/2014 | Lemme et al. |
| 8,895,296 B2 | 11/2014 | Sano et al. |
| 8,916,097 B2 | 12/2014 | Stein et al. |
| 8,921,099 B2 | 12/2014 | Ootani et al. |
| 8,986,611 B2 | 3/2015 | Lee et al. |
| 8,992,833 B2 | 3/2015 | Blecka et al. |
| 9,023,282 B2 | 5/2015 | Adachi et al. |
| 9,028,753 B2 | 5/2015 | Hegazi et al. |
| 9,028,756 B2 | 5/2015 | Yamamoto et al. |
| 9,034,639 B2 | 5/2015 | Freeman et al. |
| 9,047,545 B2 | 6/2015 | Dussi et al. |
| 9,057,714 B2 | 6/2015 | Gomm et al. |
| 9,075,055 B2 | 7/2015 | Diamond et al. |
| 9,091,656 B2 | 7/2015 | Lee et al. |
| 9,168,523 B2 | 10/2015 | Ludowise et al. |
| 9,255,865 B2 | 2/2016 | Kennedy et al. |
| 9,291,549 B2 | 3/2016 | Schwoebel et al. |
| 9,292,779 B2 | 3/2016 | Dussi et al. |
| 9,316,583 B2 | 4/2016 | Yamamoto et al. |
| 9,335,338 B2 | 5/2016 | Ochranek et al. |
| 9,341,640 B2 | 5/2016 | Shintani et al. |
| 9,352,320 B2 | 5/2016 | Corbett |
| 9,372,156 B2 | 6/2016 | Knight |
| 2001/0019826 A1 | 9/2001 | Ammann |
| 2002/0104389 A1 | 8/2002 | Hovey |
| 2003/0008385 A1* | 1/2003 | Tweedie ............... B01J 19/0046 |
| | | 435/287.2 |
| 2012/0046203 A1 | 2/2012 | Walsh et al. |
| 2012/0251389 A1 | 10/2012 | Akutsu |
| 2014/0273241 A1 | 9/2014 | Ochranek et al. |
| 2014/0319379 A1 | 10/2014 | Manian |
| 2015/0010435 A1 | 1/2015 | Matsumoto et al. |
| 2015/0010437 A1* | 1/2015 | Mellars ............ G01N 35/00732 |
| | | 422/67 |
| 2015/0010993 A1 | 1/2015 | Ingber et al. |
| 2015/0063956 A1 | 3/2015 | King et al. |
| 2015/0090866 A1 | 4/2015 | Lee et al. |
| 2015/0268259 A1 | 9/2015 | Gomm et al. |
| 2015/0276580 A1 | 10/2015 | Fukuju et al. |
| 2015/0299639 A1 | 10/2015 | Kleefstra et al. |
| 2015/0316531 A1 | 11/2015 | Tarumi et al. |
| 2015/0362431 A1 | 12/2015 | Jin Wong et al. |
| 2016/0011224 A1* | 1/2016 | Pollack ................ G01N 35/04 |
| | | 700/230 |
| 2016/0025758 A1 | 1/2016 | Yogi et al. |
| 2016/0116495 A1 | 4/2016 | Cooney et al. |
| 2016/0138071 A1 | 5/2016 | Edberg |

FOREIGN PATENT DOCUMENTS

| | | |
|---|---|---|
| CN | 1556922 A | 12/2004 |
| CN | 1611946 A | 5/2005 |
| CN | 1936587 A | 3/2007 |
| CN | 200965517 Y | 10/2007 |
| CN | 101078684 A | 11/2007 |
| CN | 101097222 A | 2/2008 |
| CN | 101151521 A | 3/2008 |
| CN | 101151534 A | 3/2008 |
| CN | 201043970 Y | 4/2008 |
| CN | 201327493 Y | 10/2009 |
| CN | 101644664 A | 2/2010 |
| CN | 201434828 Y | 3/2010 |
| CN | 201434849 Y | 3/2010 |
| CN | 102166771 A | 7/2011 |
| CN | 102224410 A | 10/2011 |
| CN | 202133672 U | 2/2012 |
| CN | 202362313 U | 8/2012 |
| CN | 202404012 U | 8/2012 |
| CN | 102667491 A | 9/2012 |
| CN | 102822678 A | 12/2012 |
| CN | 202735240 U | 2/2013 |
| CN | 202735360 U | 2/2013 |
| CN | 102998473 A | 3/2013 |
| CN | 103026238 A | 4/2013 |
| CN | 103403533 A | 11/2013 |
| CN | 103439522 A | 12/2013 |
| CN | 203519500 U | 4/2014 |
| CN | 203587503 U | 5/2014 |
| CN | 203786128 U | 8/2014 |
| CN | 203825022 U | 9/2014 |
| CN | 204086119 U | 1/2015 |
| CN | 204101459 U | 1/2015 |
| CN | 204116364 U | 1/2015 |
| CN | 104459173 A | 3/2015 |
| CN | 104777291 A | 7/2015 |
| CN | 105170203 A | 12/2015 |
| EP | 0425297 A1 | 5/1991 |
| EP | 0690309 A2 | 1/1996 |
| EP | 1055926 A2 | 11/2000 |
| EP | 1087231 A2 | 3/2001 |
| EP | 1240944 A2 | 9/2002 |
| EP | 1087231 B1 | 11/2004 |
| EP | 1477813 A1 | 11/2004 |
| EP | 1517147 A2 | 3/2005 |
| EP | 1767272 A1 | 3/2007 |
| EP | 1867978 A1 | 12/2007 |
| EP | 1867997 A1 | 12/2007 |
| EP | 1873530 A1 | 1/2008 |
| EP | 1767272 B1 | 3/2010 |
| EP | 1508613 B1 | 10/2010 |
| EP | 1639368 B1 | 10/2011 |
| EP | 2502082 B1 | 9/2012 |
| WO | 2008007923 A1 | 1/2008 |
| WO | 2015053795 A1 | 4/2015 |

OTHER PUBLICATIONS

International Preliminary Report on Patentability for PCT/US2016/039559, dated Dec. 26, 2017, 8 pages.
International Preliminary Report on Patentability for PCT/US2016/039581, dated Dec. 26, 2017, 8 pages.

* cited by examiner

US 10,288,633 B2

REACTION VESSEL MOVING MEMBER FOR MOVING REACTION VESSELS FROM A PROCESSING TRACK TO A ROTATING DEVICE IN A DIAGNOSTIC ANALYZER

CROSS-REFERENCE TO RELATED APPLICATIONS

This application claims benefit of priority to U.S. provisional application No. 62/185,546, filed on Jun. 26, 2015, which is incorporated by reference in its entirety.

FIELD OF THE DISCLOSURE

This disclosure relates to reaction vessel moving members for moving reaction vessels from processing tracks to optical readers in diagnostic analyzers in order to detect conditions of samples contained within the reaction vessels.

BACKGROUND

Current diagnostic analyzers often use a large number of costly, space-consuming, complex, and high-maintenance devices to transfer reaction vessels into detection systems in order to detect conditions of samples held within the reaction vessels. Other diagnostic analyzers have shutter devices to place samples in a dark environment for optical analysis; however, the shutter devices may allow external light leakage. Other current diagnostic analyzers have varying issues.

A diagnostic analyzer and method of use is needed to overcome or reduce one or more issues associated with one or more of the current diagnostic analyzers.

SUMMARY

In one embodiment, a diagnostic analyzer is disclosed. The diagnostic analyzer includes a rotating device, a first optical reader, and a second optical reader. The rotating device includes a first darkened compartment, a second darkened compartment, and an optical path along which the first darkened compartment and the second darkened compartment travel. The first optical reader is operable to read the first darkened compartment and the second optical reader is operable to read the second darkened compartment.

In another embodiment, a diagnostic analyzer is disclosed. The diagnostic analyzer includes a darkened optical reading area, a processing track, and a reaction vessel moving member. The processing track is disposed below the darkened optical reading area. The reaction vessel moving member is configured to move a reaction vessel carried by the processing track out of the processing track and into the darkened optical reading area.

In still another embodiment, a method is disclosed of taking reading of samples using a diagnostic analyzer. In one step, a rotating device is rotated along an optical path. In another step, a first darkened compartment of the rotating device is read with a first optical reader in order to take a reading of a first sample. In yet another step, a second darkened compartment of the rotating device is read with a second optical reader in order to take a reading of a second sample.

The scope of the present disclosure is defined solely by the appended claims and is not affected by the statements within this summary.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

DETAILED DESCRIPTION

Figure 1:
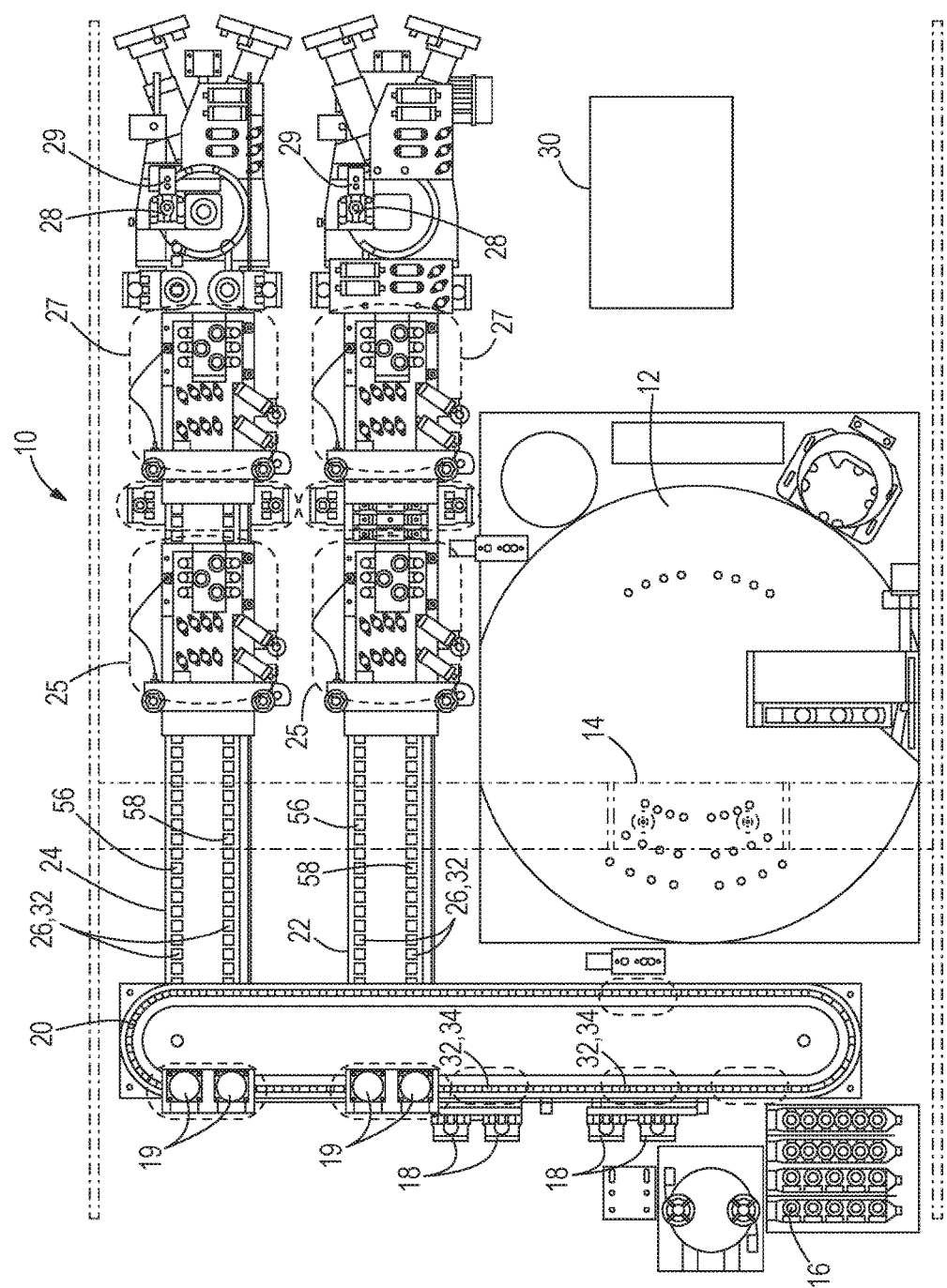
FIG. 1 illustrates a top view of one embodiment of a diagnostic analyzer.

FIG. 1 illustrates a top view of one embodiment of a diagnostic analyzer 10. The diagnostic analyzer 10 in part comprises a reagent carousel 12, a pipetting device 14, a sample supply device 16, reaction vessel supply devices 18, reaction vessel exchanger devices 19, an incubation track 20, processing tracks 22 and 24, wash devices 25 and 27, reaction vessel transfer devices 28, detection devices 29, and at least one processor 30. It is noted that the at least one processor 30 may be used to control any of the components of the diagnostic analyzer 10.

The at least one processor 30 controls the incubation track 20 to rotate it clockwise as needed. The reaction vessel supply devices 18 are controlled by the at least one processor 30 to deliver reaction vessels 32 into incubation track slots 34 of the incubation track 20. The pipetting device 14 is then controlled by the at least one processor 30 to pipette reagent from the reagent carousel 12 into the reaction vessels 32 in the incubation track slots 34. The pipetting device 14 is then controlled by the at least one processor 30 to pipette samples from the sample supply device 16 into the reaction vessels 32. The reaction vessel exchanger devices 19 are then controlled to transfer the reaction vessels 32 from the incubation track slots 34 of the incubation track 20 into processing track slots 26 of the processing tracks 22 and 24.

The at least one processor 30 is used to rotate the processing tracks 22 and 24 counter-clockwise as needed. The wash devices 25 are then controlled by the at least one processor 30 to wash the samples in the reaction vessels 32 within the processing track slots 26 of the processing tracks 22 and 24. The pipetting device 14 is then controlled by the at least one processor 30 to pipette reagent from the reagent carousel 12 into the reaction vessels 32 in the processing track slots 26 of the processing tracks 22 and 24. The wash devices 27 are then controlled by the at least one processor 30 to wash the samples in the reaction vessels 32 within the processing track slots 26 of the processing tracks 22 and 24. The reaction vessel transfer devices 28 are then controlled by the at least one processor 30 to transfer the reaction vessels 32 from the processing track slots 26 of the processing tracks 22 and 24 into the detection devices 29. The detection devices 29 are then controlled by the at least one processor 30 to detect properties of the samples within the reaction vessels 32. In other embodiments, the components and function of the diagnostic analyzer 10 may vary.

Figure 2:
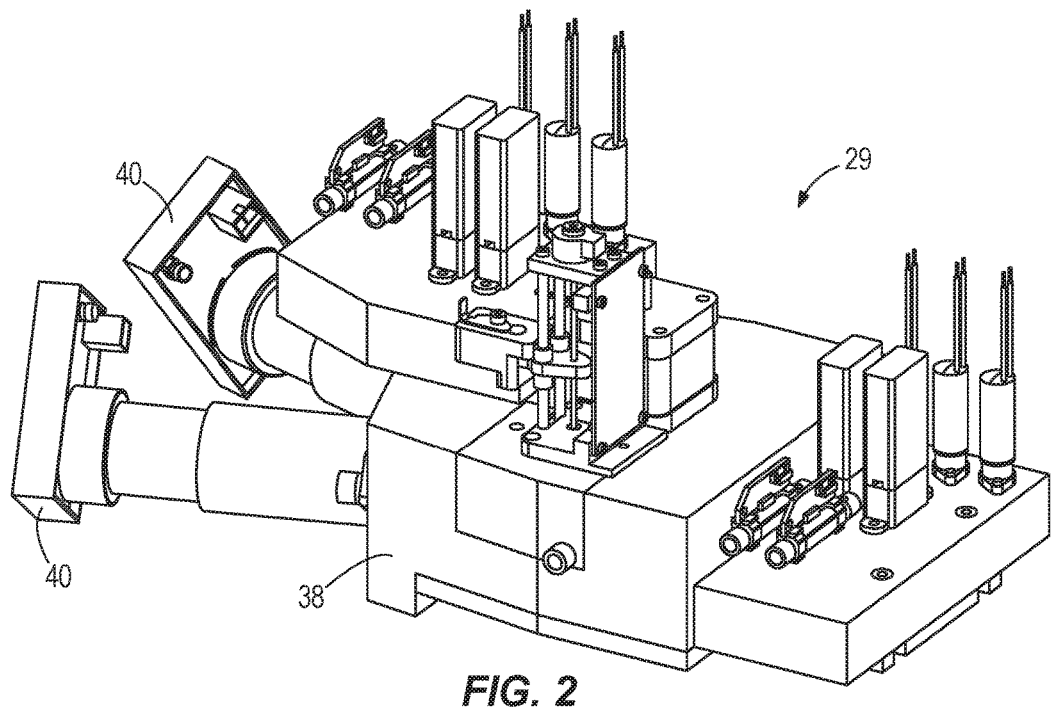
FIG. 2 illustrates a top perspective view of one of the detection devices of the diagnostic analyzer of the embodiment of FIG. 1.

FIG. 2 illustrates a top perspective view of one of the detection devices 29 of the embodiment of FIG. 1. The detection device 29 comprises a housing 38 and optical readers 40. The housing 38 is designed to keep the reaction vessels 32 (see FIG. 1) in a darkened environment when disposed within the housing 38. The optical readers 40 may comprise first and second optical sensors. In other embodiments, the optical readers 40 may vary in number, location, configuration, orientation, or position.

Figure 3:
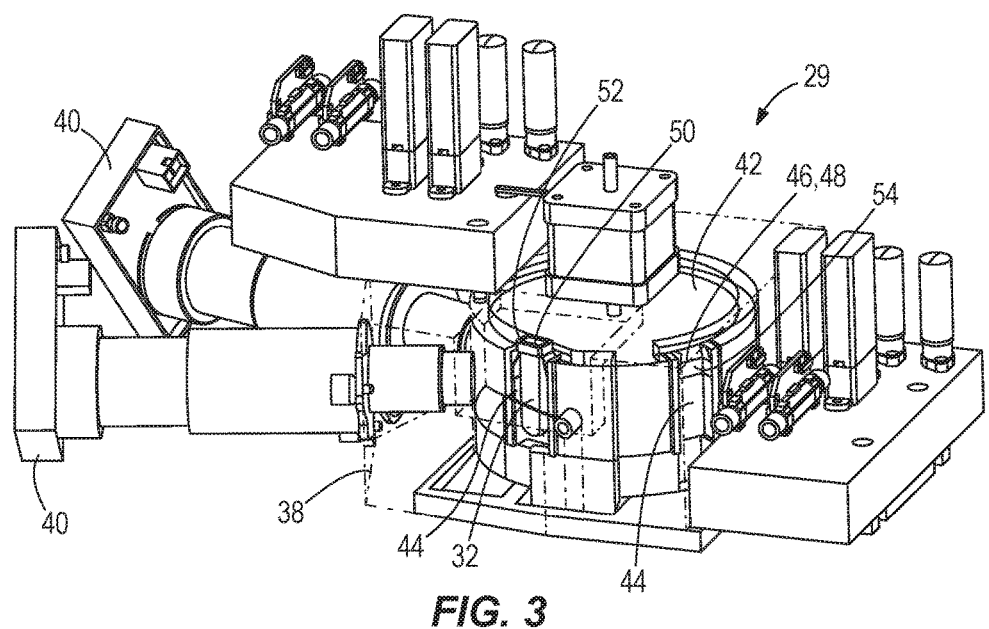
FIG. 3 illustrates an internal perspective view of the detection device shown in FIG. 2.

FIG. 3 illustrates an internal perspective view of the detection device 29 shown in FIG. 2. As shown, disposed within the housing 38 is a rotating device 42 comprising spaced-apart darkened optical reading areas which comprise spaced-apart darkened compartments 44. The term "darkened optical reading area" is defined as a darkened area at which an optical reading is taken. In other embodiments, the spaced-apart darkened optical reading areas may vary in number, location, configuration, and orientation. The rotating device 42 comprises an optical path along which the spaced-apart darkened components 44 travel. This optical path comprises the circular path that the spaced-apart darkened components 44 travel when the rotating device 42 rotates. In other embodiments, the optical path of the darkened optical reading area may vary in configuration, orientation, direction, shape, and size. The rotating device 42 may comprise a rotating turret. In other embodiments, the rotating device 42 may vary. The spaced-apart darkened compartments 44 are each configured to hold one of the reaction vessels 32 within the darkened compartment 44. Each darkened compartment 44 comprises a reaction vessel holding member 46 for holding a reaction vessel 32 within the darkened compartment 44. The reaction vessel holding member 46 comprises a ledge 48 configured to hold a portion 50 of the reaction vessel 32 in place against the ledge 48 so that the reaction vessel 32 is held within the darkened compartment 44. The portion 50 of the reaction vessel 32 may comprise a top shoulder 52 of the reaction vessel 32 which may abut over and against the ledge 48 of the darkened compartment 44. In other embodiments, the reaction vessel holding member 46 may vary in its type, structure, configuration, orientation, or function. For instance, in one embodiment, the reaction vessel holding member 46 may comprise pivoting fingers as discussed below for the embodiment of FIGS. 11-14. Each darkened compartment 44 further comprises a push-out member 54 to push the reaction vessel 32 away from the reaction vessel holding member 46 so that the reaction vessel 32 passes out of the darkened compartment 44 when the optical readers 40 have completed their readings.

FIGS. 4-10 illustrate chronological movement, for the embodiment of FIGS. 1-4, of the reaction vessels 32 from the processing tracks 22 and 24 into one of the detection device 29 to obtain readings of samples within the reaction vessels 32, and subsequently out of the detection device 29 after the readings have been completed.

Figure 4:
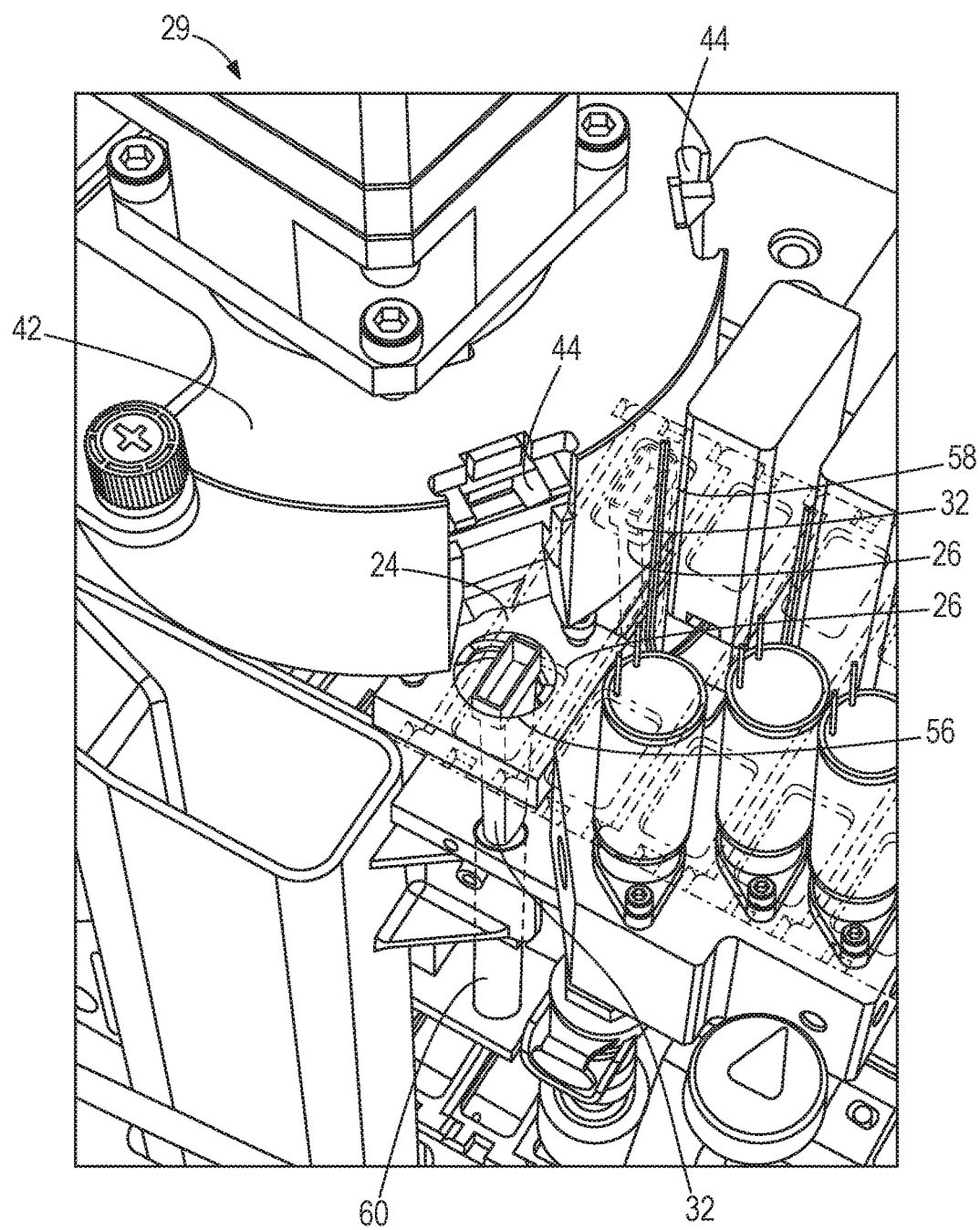
FIG. 4 illustrates a top perspective view of a processing track of the diagnostic analyzer of FIG. 1 having moved counter-clockwise in order to dispose reaction vessels held in processing track slots of parallel lanes of the processing track in vertical alignment with spaced-apart darkened compartments of a rotating device while a reaction vessel moving member is disposed in a lowered vertically aligned position.

FIG. 4 illustrates a top perspective view of the processing track 24 having moved counter-clockwise in order to dispose the reaction vessels 32 held in the processing track slots 26 of the parallel lanes 56 and 58 (see FIG. 1) of the processing track 24 in vertical alignment with the spaced-apart darkened compartments 44 of the rotating device 42. Reaction vessel moving member 60 is disposed in a lowered position under and apart in vertical alignment from a reaction vessel 32 held by one of the processing track slots 26 of lane 56 of the processing track 24 and in vertical alignment with one of the spaced-apart darkened compartments 44 of the rotating device 42. The reaction vessel moving member 60 comprises a shaft. In other embodiments, the reaction vessel moving member 60 may vary.

An identical reaction vessel moving member which is hidden from view in FIG. 4 is also disposed under and apart in vertical alignment from another reaction vessel 32 held by one of the processing track slots 26 of lane 58 of the processing track 24 and in vertical alignment with the other of the spaced-apart darkened compartments 44 of the rotating device 42. It is noted that although FIGS. 4-10 only show the operation of one of the detection devices 29 and its reaction vessel moving members 60 that the other detection device 29 located over the parallel lanes 56 and 58 of the processing track 22 (see FIG. 1) and its respective reaction vessel moving members are identical in form and function.

Figure 5:
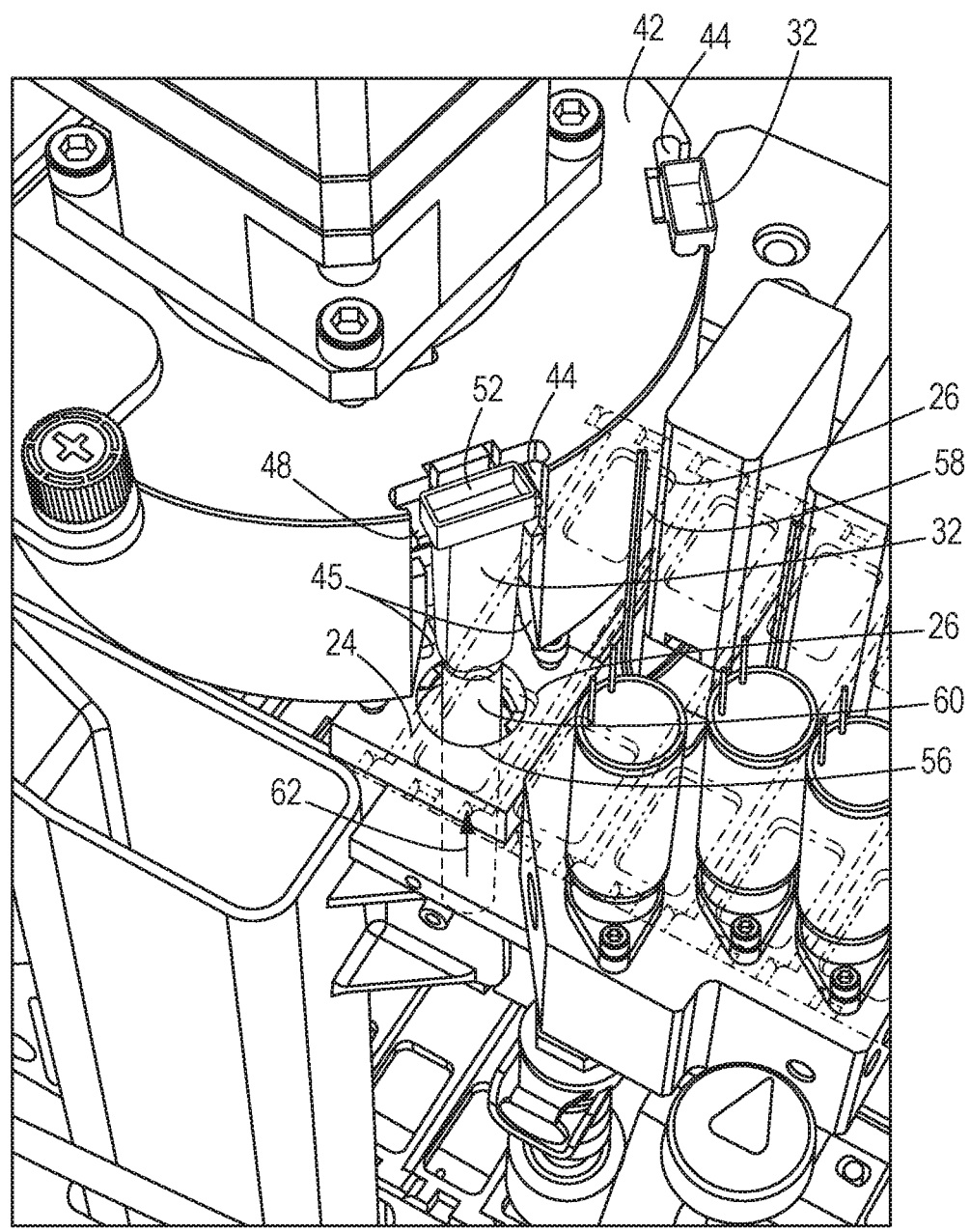
FIG. 5 illustrates a top perspective view of the processing track of FIG. 4 with the reaction vessel moving member having moved from its lowered position of FIG. 4, through an intermediate position disposed against a reaction vessel within the processing track slot, to a raised position pushing the reaction vessel out of the processing track slot of the processing track and into the aligned darkened compartment of the rotating device.

FIG. 5 illustrates a top perspective view of the processing track 24 of FIG. 4 with the reaction vessel moving member 60 having moved in direction 62 from the lowered position of FIG. 4, through an intermediate position disposed against the reaction vessel 32 within the processing track slot 26, to a raised position pushing the reaction vessel 32 out of the processing track slot 26 of lane 56 of the processing track 24 and into the aligned darkened compartment 44 of the rotating device 42. It is noted that as the reaction vessel moving member 60 moved in direction 62 thereby pushing the reaction vessel 32 into the darkened compartment 44, that the reaction vessel 32 rotated into the correct alignment position within the darkened compartment 44 due to the guide members 45 of the darkened compartment 44. In other embodiments, one or more guide members 45 of any type, configuration, orientation, or location (inside or outside of the darkened compartment 44 including below the processing track 24) may be used to rotate/guide the reaction vessel 32 into the darkened compartment 44. The top shoulder 52 of the reaction vessel 32 has been disposed over and against the ledge 48 of the darkened compartment 44 to hold the reaction vessel 32 in place within the darkened compartment 44. The identical movement of the hidden reaction vessel moving member happens with respect to the other spaced-apart darkened compartment 44 of the rotating device 42 in order to push the aligned reaction vessel 32 of the other lane 58 of the processing track 24 into the other spaced-apart darkened compartment 44. In other embodiments, the reaction vessel moving members 60 may be disposed in varying orientations and configurations relative to the processing track 24 and the rotating device 42 and may move between first, second, and third positions to move the reaction vessels 32 out of the processing track slots 26 of the processing track 24 into the darkened compartments 44 of the rotating device 42.

Figure 6:
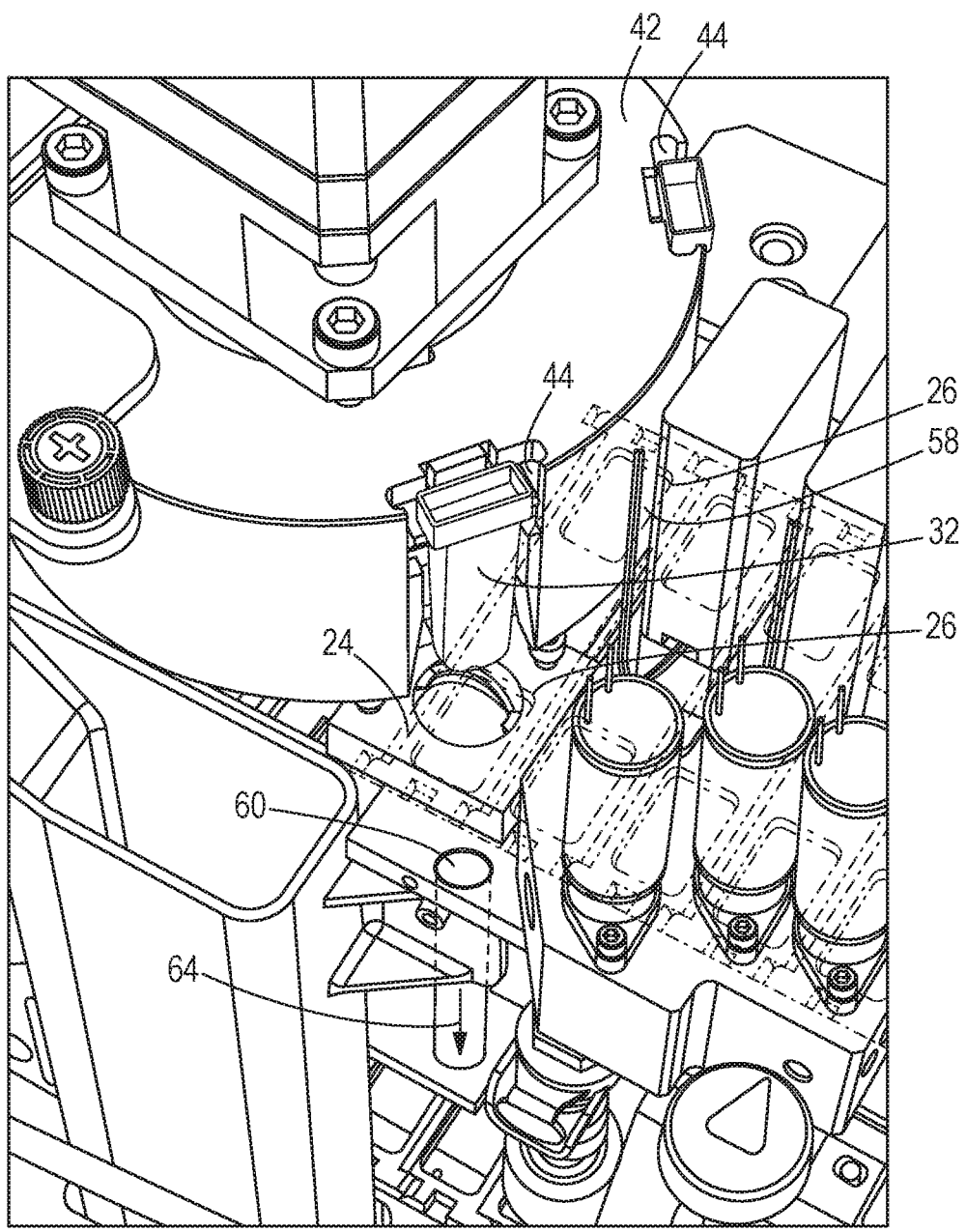
FIG. 6 illustrates a top perspective view of the processing track of FIG. 5 with the reaction vessel moving member having moved away from the reaction vessel, leaving the reaction vessel disposed in a fixed position within the darkened compartment of the rotating device, and back through the processing track slot of the processing track into its original position disposed below and apart from the processing track.

FIG. 6 illustrates a top perspective view of the processing track 24 of FIG. 5 with the reaction vessel moving member 60 having moved in direction 64 away from the reaction vessel 32, which is disposed in the fixed position within the darkened compartment 44 of the rotating device 42, and back through the processing track slot 26 of the processing track 24 into its original position disposed below and apart from the processing track 24. The identical movement of the hidden reaction vessel moving member associated with the processing track slots 26 of lane 58 happens with respect to the other spaced-apart darkened compartment 44 of the rotating device 42.

Figure 7:
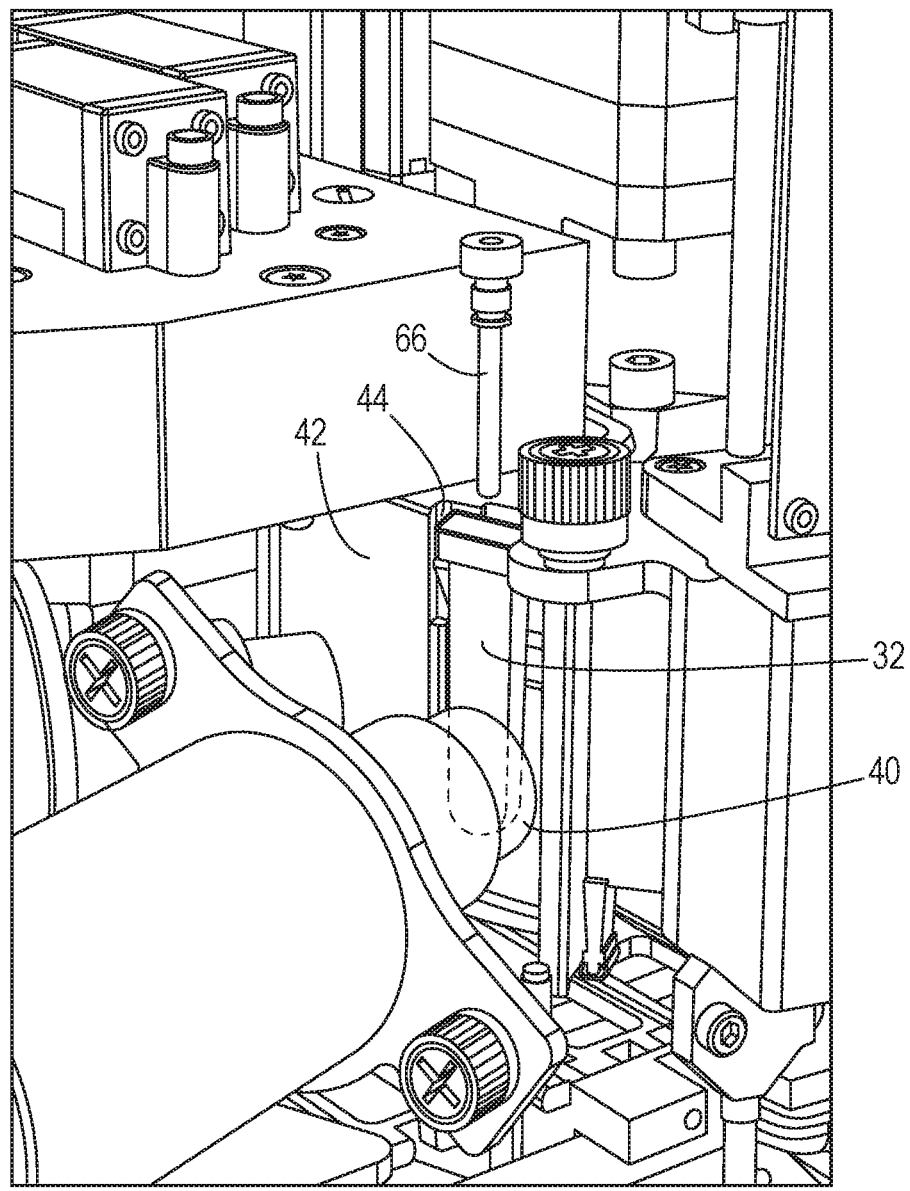
FIG. 7 illustrates a top perspective view of the device of FIG. 6 having rotated counter-clockwise to dispose the darkened compartment and the reaction vessel fixed within it in alignment with an optical reader.

FIG. 7 illustrates a top perspective view of the rotating device 42 of FIG. 6 having rotated counter-clockwise to dispose the darkened compartment 44 and the reaction vessel 32 carried within it into alignment with the optical reader 40. At this time, trigger pipettor 66 dispenses a trigger-solution into reaction vessel 32, and then the optical reader 40 takes a reading of the sample disposed within the reaction vessel 32. The other spaced-apart optical reader which is hidden from view (shown in FIGS. 2 and 3) takes a reading of the reaction vessel held by the other spaced-apart darkened compartment which is also hidden from view after an identical trigger pipettor dispenses trigger-solution into the reaction vessel held within the other spaced-apart darkened compartment. It is noted that each of the optical readers are configured to only take readings of the reaction vessels held by their respective assigned spaced-apart darkened compartment so that only one reading is taken of the reaction vessels held by the space-apart darkened compartments. In such manner, the first optical reader is operable to read the first darkened compartment and the second optical reader is operable to read the second darkened compartment.

Figure 8:
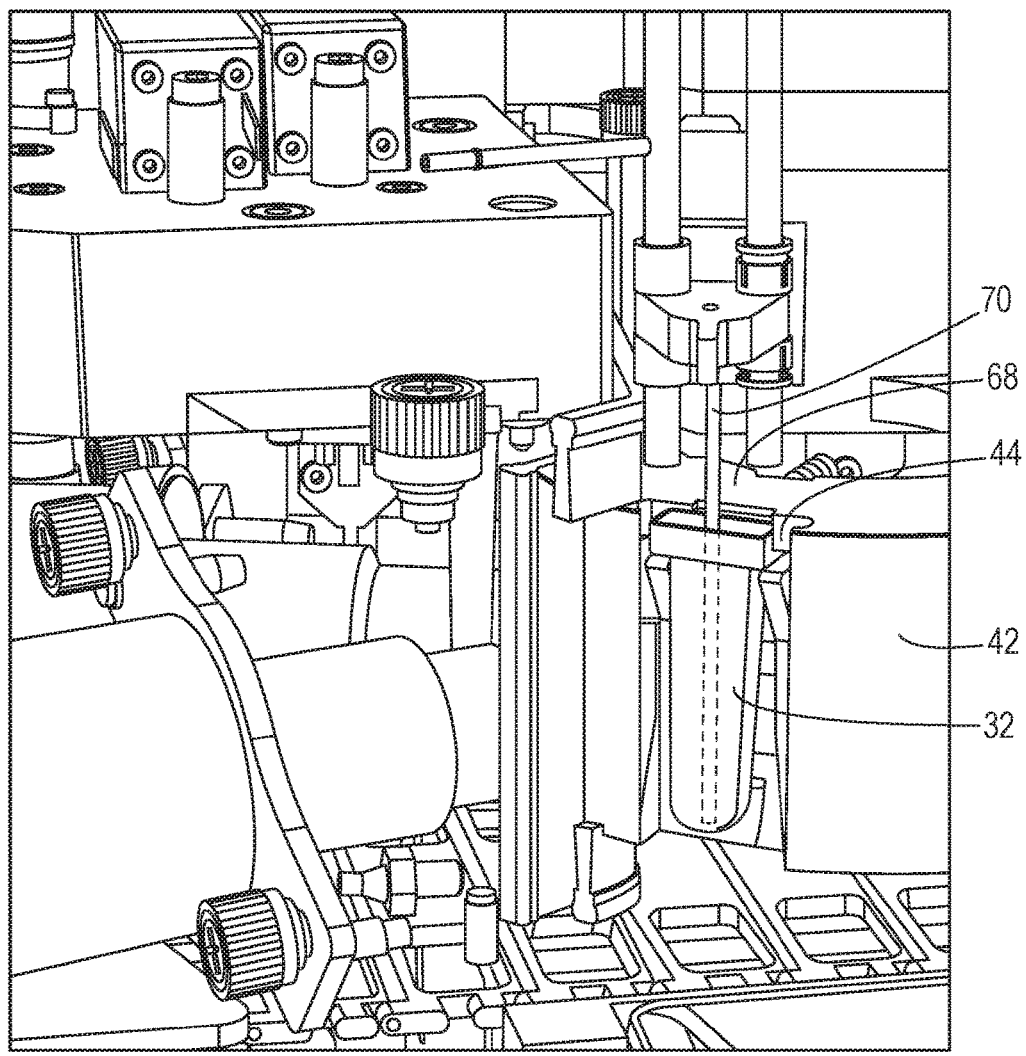
FIG. 8 illustrates a top perspective view of the device of FIG. 7 having rotated counter-clockwise to dispose the darkened compartment and the reaction vessel fixed within it at an aspiration location.

FIG. 8 illustrates a top perspective view of the rotating device 42 of FIG. 7 having rotated counter-clockwise to dispose the darkened compartment 44 and the reaction vessel 32 carried within it at aspiration location 68. An aspiration pipettor 70 aspirates the contents of the reaction vessel 32 and disposes of those contents. The rotating device 42 also locates the other spaced-apart darkened compartment which is hidden from view at another aspiration location at which another aspiration pipettor aspirates the contents of the reaction vessel within that hidden darkened compartment and disposes of those contents. In another embodiment, the reaction vessels 32 can be aspirated by the same aspiration pipettor 70 at the same aspiration location 68.

Figure 9:
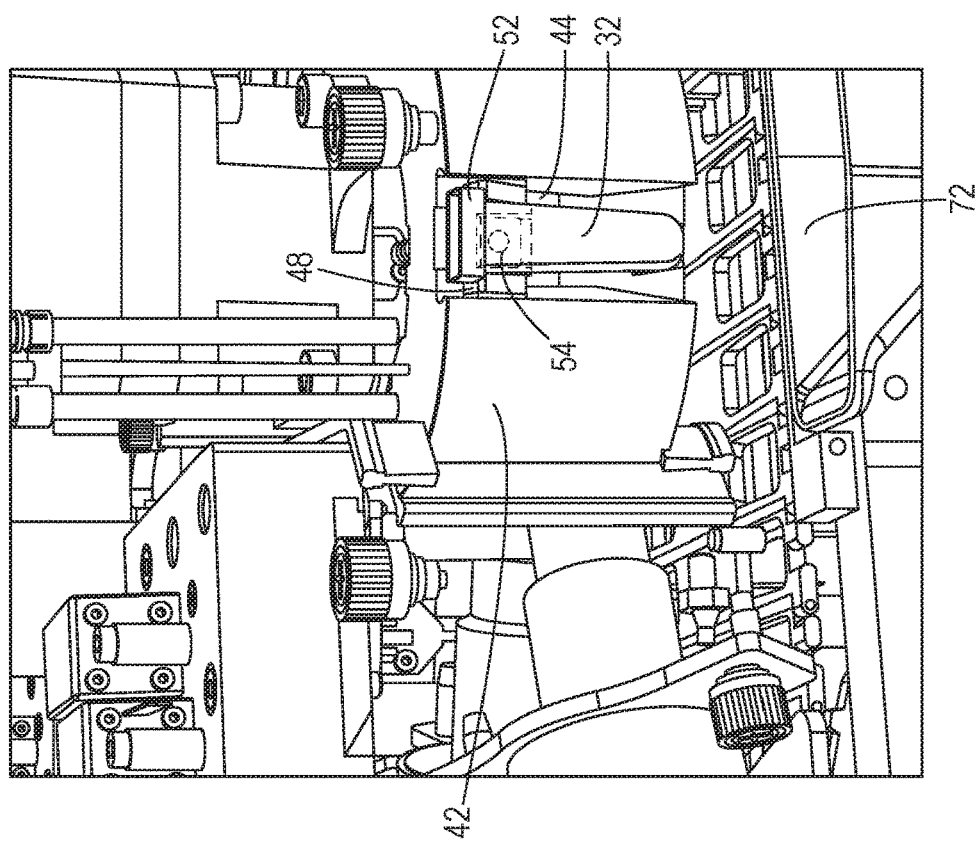
FIG. 9 illustrates a top perspective view of the device of FIG. 8 having rotated counter-clockwise to dispose the darkened compartment and the reaction vessel fixed within it at disposal location.

FIG. 9 illustrates a top perspective view of the rotating device 42 of FIG. 8 having rotated counter-clockwise to dispose the darkened compartment 44 and the reaction vessel 32 carried within it at disposal location 72. Push-out member 54 pushes the top shoulder 52 of the reaction vessel 32 away from and off of the ledge 48 of the darkened compartment 44. The rotating device 42 will later in time rotate counter-clockwise to move the hidden darkened compartment and the reaction vessel carried within it to the disposal location 72 at which time the hidden push-out member of the hidden darkened compartment will push the reaction vessel away and off of the ledge of the hidden darkened compartment.

Figure 10:
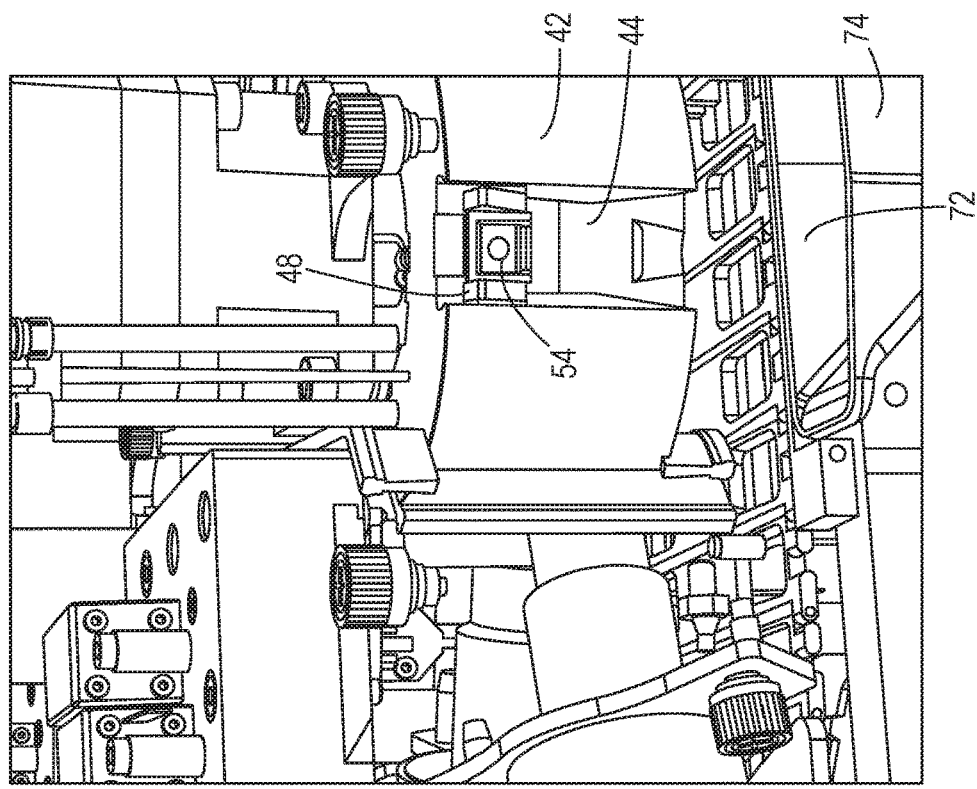
FIG. 10 illustrates a top perspective view of the device of FIG. 9 showing the reaction vessel having fallen through the darkened compartment into a disposal container as a result of a push-out member having pushed the reaction vessel off a ledge of the darkened compartment.

FIG. 10 illustrates a top perspective view of the rotating device 42 of FIG. 9 showing the reaction vessel 32 (hidden from this view but shown in FIG. 9) having fallen through the darkened compartment 44 into disposal container 74 as a result of the push-out member 54 having pushed the reaction vessel 32 off the ledge 48 of the darkened compartment 44. Later when the rotating device 42 has rotated so that the hidden darkened compartment is disposed at disposal location 72 the push-out member of the hidden darkened compartment will push the reaction vessel disposed in the hidden darkened compartment away and off of the ledge of the hidden darkened compartment so that the reaction vessel falls through the hidden darkened compartment and into disposal container 74.

The rotating device 42 will continue to rotate counter-clockwise in order to repeat the steps of FIGS. 4-10 to read the samples disposed within all of the reaction vessels 32 carried by the processing track slots 26 of both lanes 56 and 58 of the processing track 24 shown in FIG. 1. Similarly, the rotating device of the detection device 29 disposed over the processing track slots 26 of lanes 56 and 58 of processing track 22 (shown in FIG. 1) will also repeat these same steps to read the samples disposed within all of the reaction vessels 32 carried by their processing track slots 26.

In other embodiments, the diagnostic analyzer 10 of FIGS. 1-10 may vary in form or function. For instance, one or more of the components of the diagnostic analyzer 10 may be varied or not present, or an additional component may be added.

Figure 11:
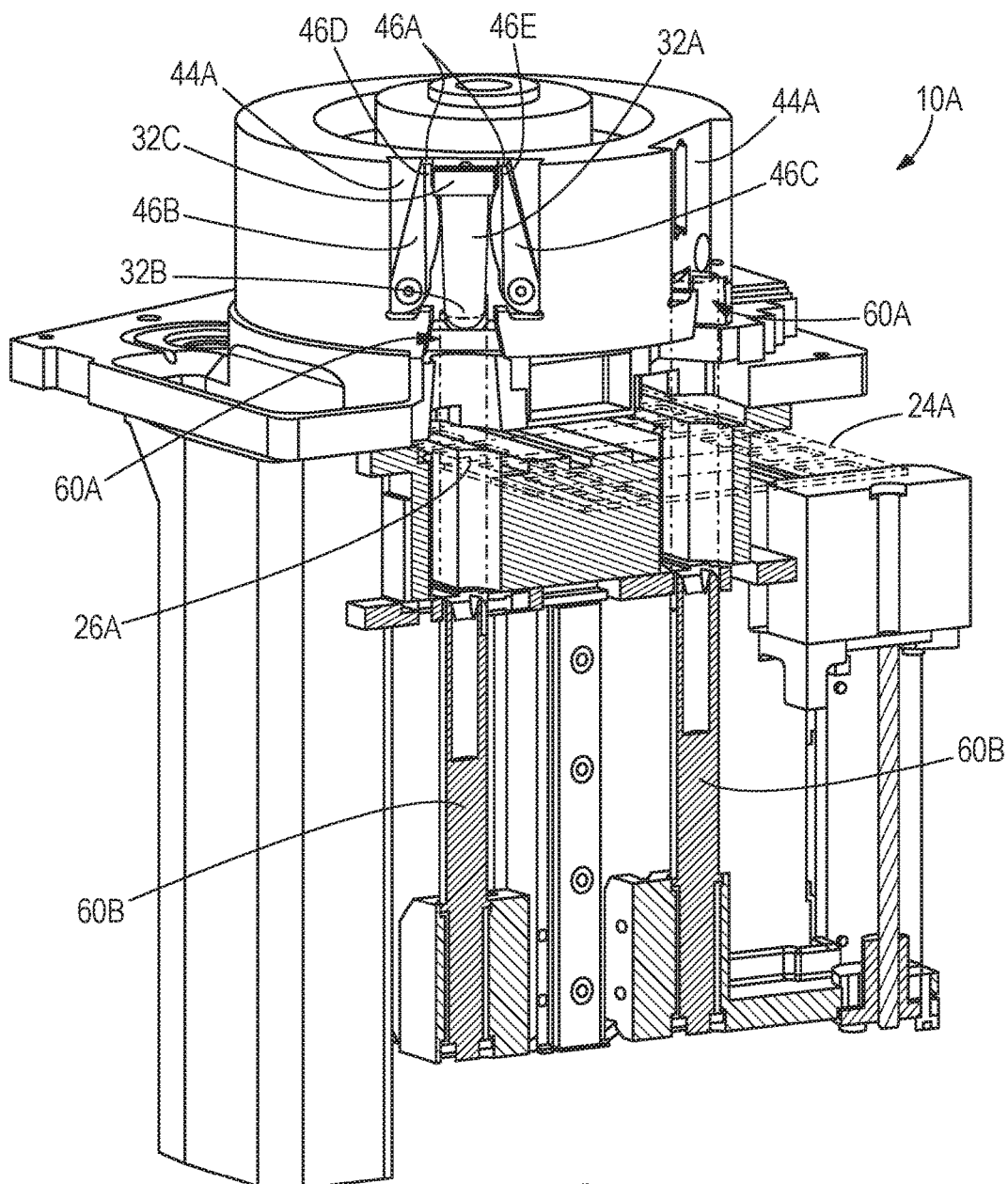
FIG. 11 illustrates a side perspective view of one embodiment of another diagnostic analyzer showing some of its.
Figure 12:
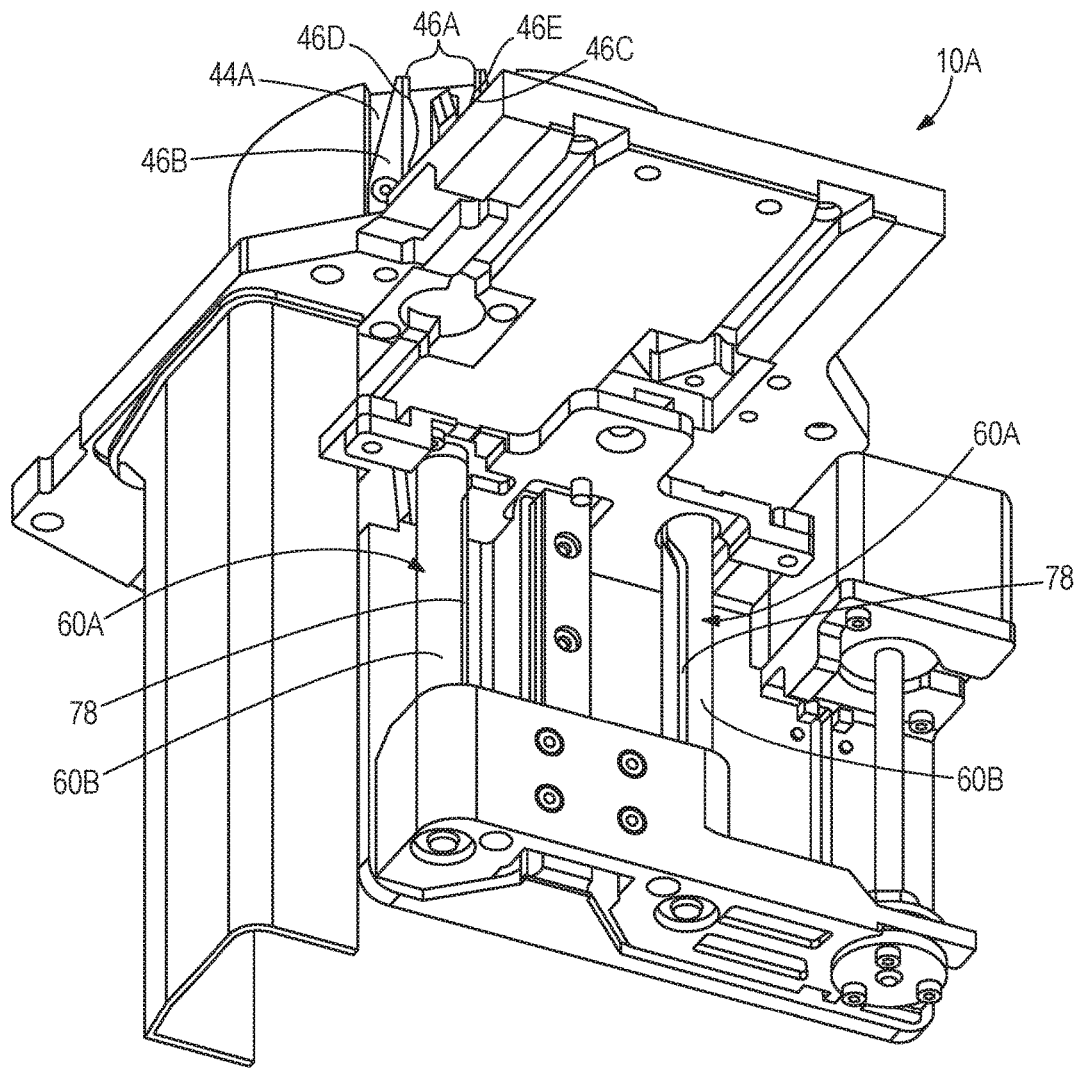
FIG. 12-14 illustrate varying perspective views of particular components of the diagnostic analyzer of the embodiment of FIG. 11.
Figure 13:
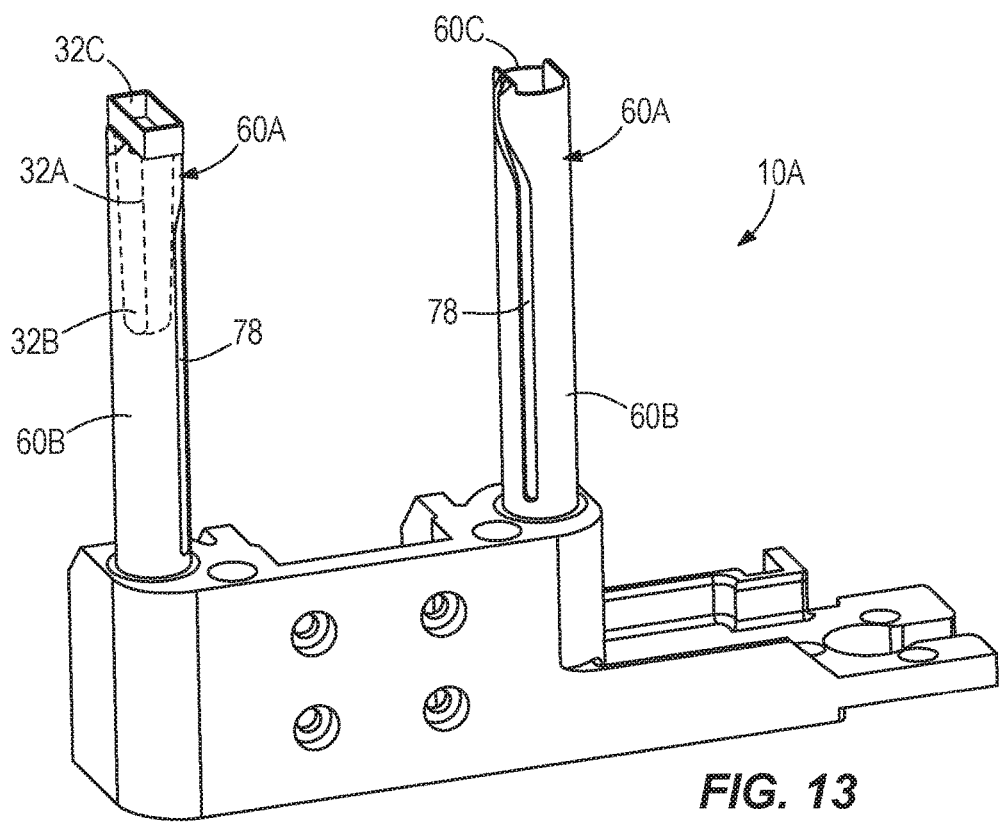
Figure 14:
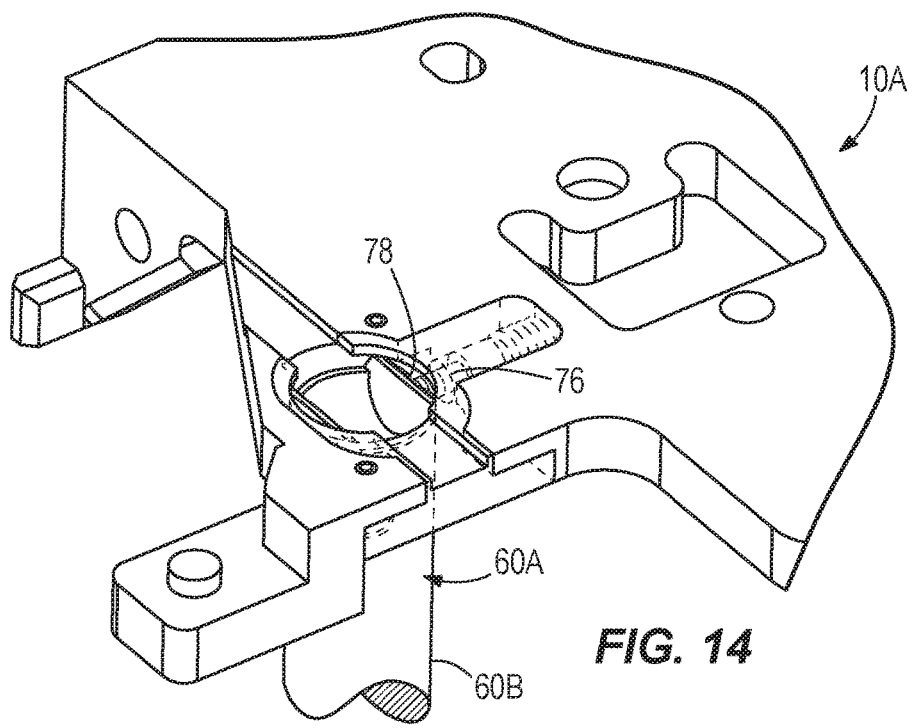

FIG. 11 illustrates a side perspective view of one embodiment of another diagnostic analyzer 10A showing some of its components. FIGS. 12-14 illustrate varying perspective views of particular components of the diagnostic analyzer 10A of the embodiment of FIG. 11. The diagnostic analyzer 10A functions similarly as the diagnostic analyzer 10 of the embodiment of FIGS. 1-10 with a few exceptions identified in the following discussion of FIGS. 11-14.

As shown collectively in FIGS. 11-14, the reaction vessel moving member 60A for moving between the lowered, intermediate, and raised positions to move the reaction vessel 32A out of the processing track slot 26A of the processing track 24A into the darkened compartment 44A comprises a hollow shaft 60B which is sized to allow a bottom portion 32B of the reaction vessel 32A to be disposed within an interior of the hollow shaft 60B. The darkened compartment 44A comprises a darkened optical reading area. As best shown in FIG. 13, the hollow shaft 60B comprises an anti-rotation member 60C to prevent the reaction vessel 32A from rotating relative to the hollow shaft 60B. The anti-rotation member 60C comprises a pocket which a ledge 32C of the reaction vessel 32A sits within. In other embodiments, the anti-rotation member 60C of the hollow shaft 60B may vary.

As best shown in FIGS. 12 and 14, a first mating member 76 and a second mating member 78 are mated causing the hollow shaft 60B to rotate as it moves between the lowered and the raised positions in order to precisely locate the reaction vessel 32A within the darkened compartment 44A at the reaction vessel holding member 46A. The first mating member 76 comprises a fixed pin and the second mating member 78 comprises a patterned groove disposed in an exterior of the hollow shaft 60B.

The reaction vessel holding member 46A comprises a plurality of pivoting members 46B and 46C which have an open position shown in FIG. 12 in which the pivoting members do not hold the reaction vessel 32A within the darkened compartment 44A and a closed position shown in FIG. 11 in which the pivoting members 46B and 46C hold the reaction vessel 32A within the darkened compartment 44A. When the hollow shaft 60B rotates to locate the reaction vessel 32A within the darkened compartment 44A the hollow shaft 60B abuts against the pivoting members 46B and 46C forcing them to pivot away from one another into their open position. Subsequently, at its top point the hollow shaft 60B locates the ledge 32C of the reaction vessel 32A against the top portions 46D and 46E of the pivoting members 46B and 46C. As shown in FIG. 11, the hollow shaft 60B then retracts from the darkened compartment 44A allowing the pivoting members 46B and 46C to come towards one another into their closed position so that the top portions 46D and 46E of the pivoting members 46B and 46C are left holding the ledge 32C of the reaction vessel 32A in a fixed position within the darkened compartment 44A.

In other embodiments, the diagnostic analyzer 10A of FIGS. 11-14 may vary in form or function. For instance, one or more of the components of the diagnostic analyzer 10A may be varied or not present, or an additional component may be added.

Figure 15:
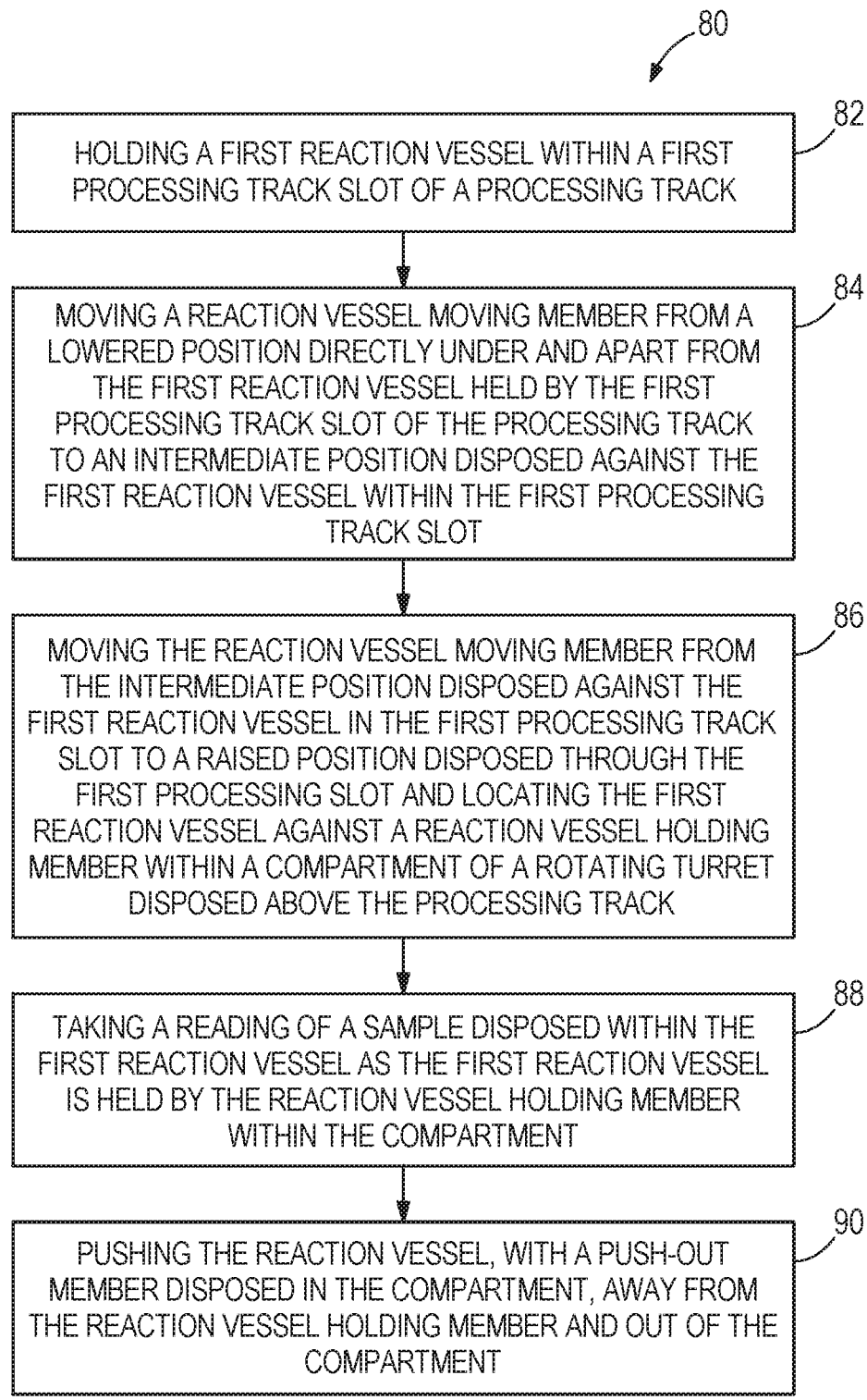
FIG. 15 illustrates a flowchart illustrating one embodiment of a method of taking a reading of a sample using a diagnostic analyzer.

FIG. 15 illustrates a flowchart illustrating one embodiment of a method 80 of taking a reading of a sample using a diagnostic analyzer. The method 80 may utilize any of the diagnostic analyzers of the instant disclosure. In other embodiments, the method 80 may utilize varying diagnostic analyzers.

In step 82, a first reaction vessel is held within a first processing track slot of a processing track. In step 84, a reaction vessel moving member is moved from a lowered position directly under and apart from the first reaction vessel held by the first processing track slot of the processing track to an intermediate position disposed against the first reaction vessel within the first processing track slot. In one embodiment, the reaction vessel moving member comprises a shaft. In another embodiment, step 84 comprises disposing a bottom portion of the first reaction vessel within a hollow interior of a shaft with an anti-rotation member of the shaft preventing the first reaction vessel from rotating relative to the shaft. In one embodiment, the anti-rotation member of the shaft may comprise a pocket of the shaft. In other embodiments, the anti-rotation member of the shaft may vary.

In step 86, the reaction vessel moving member is moved from the intermediate position disposed against the first reaction vessel in the first processing track slot to a raised position disposed through the first processing slot and locating the first reaction vessel against a reaction vessel holding member within a darkened compartment of a rotating device disposed above the processing track. The darkened compartment comprises a darkened optical reading area. The rotating device may comprise a turret. In other embodiments, the rotating device may vary. The reaction vessel holding member holds the first reaction vessel within the darkened compartment.

In one embodiment, step 86 comprises locating the first reaction vessel against a ledge of the darkened compartment. In another embodiment, step 86 comprises pivoting at least one pivoting member from an open position in which the at least one pivoting member does not hold the first reaction vessel within the darkened compartment to a closed position in which the at least one pivoting member holds the first reaction vessel within the darkened compartment. In still another embodiment, step 86 comprises a first mating member and a second mating member causing a shaft to rotate as it moves between a lowered and raised position. The first mating member and the second mating member may comprise a pin and a groove. In other embodiments, the first and second mating members may vary.

In step 88, a reading of a sample disposed within the first reaction vessel is taken as the first reaction vessel is held by the reaction vessel holding member within the darkened compartment. In one embodiment, step 88 comprises a processor controlling a first optical reader so that the first optical reader only takes readings within a first darkened compartment of the rotating device, and the processor controlling a second optical reader so that the second optical reader only takes readings within a second darkened compartment of the rotating device. In step 90, a push-out member disposed in the darkened compartment pushes the reaction vessel away from the reaction vessel holding member and out of the darkened compartment.

In other embodiments, one or more steps of the method 80 may vary in substance or in order, one or more steps of the method 80 may not be followed, or one or more additional steps may be added to the method 80.

Figure 16:
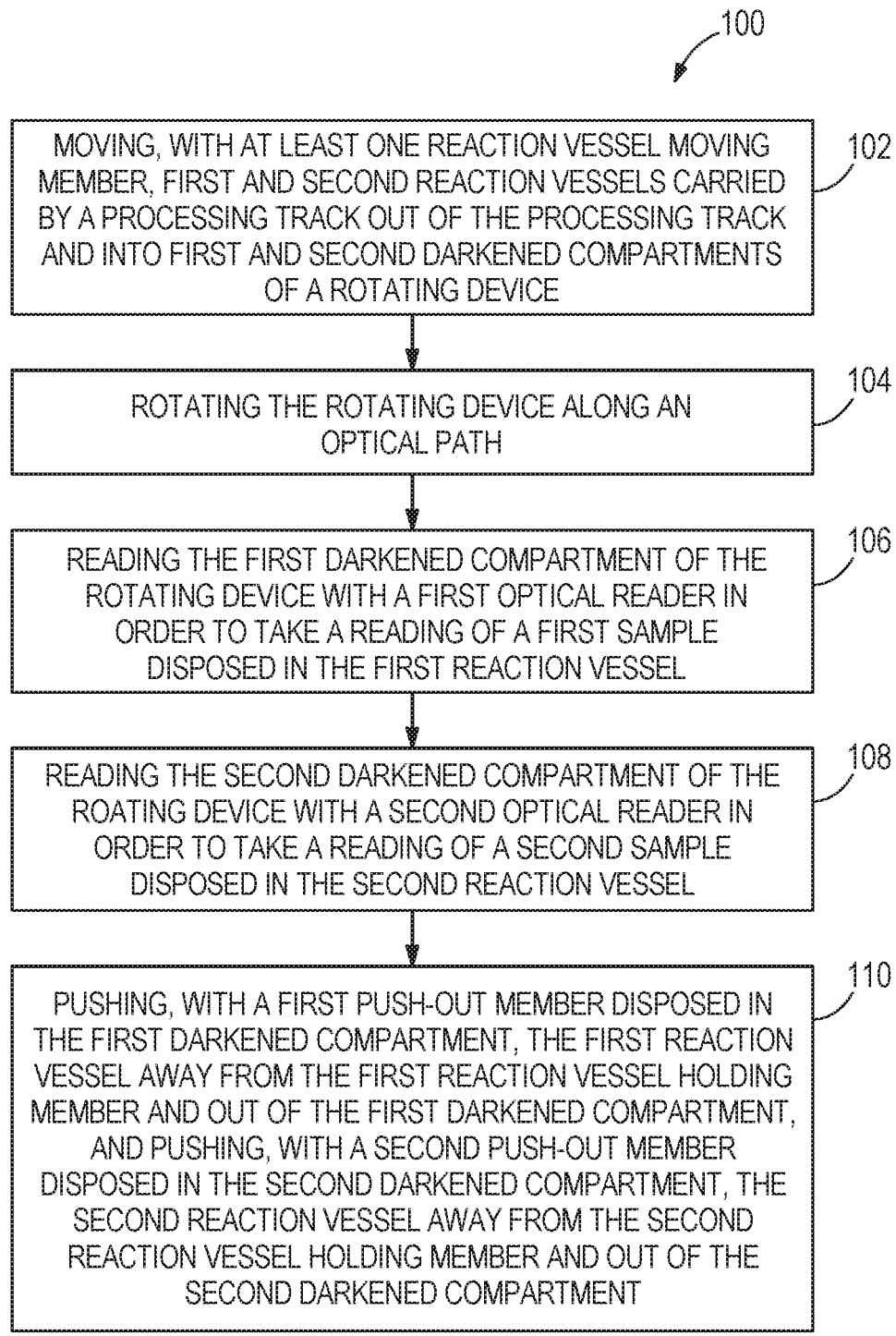
FIG. 16 illustrates a flowchart illustrating another embodiment of a method of taking readings of samples using a diagnostic analyzer.

FIG. 16 illustrates a flowchart illustrating one embodiment of a method 100 of taking readings of samples using a diagnostic analyzer. The method 100 may utilize any of the diagnostic analyzers of the instant disclosure. In other embodiments, the method 100 may utilize varying diagnostic analyzers.

In step 102, at least one reaction vessel moving member moves first and second reaction vessels carried by a processing track out of the processing track and into first and second darkened compartments of a rotating device. The first and second darkened compartments comprises darkened optical reading areas. In one embodiment, step 102 comprises at least one shaft moving the reaction vessels by disposing bottom portions of the reaction vessels within a hollow interior of the at least one shaft, and an anti-rotation member of the at least one shaft preventing the reaction vessels from rotating relative to the at least one shaft. The anti-rotation member may comprise a pocket of the at least one shaft. In other embodiments, the anti-rotation member may vary. In one embodiment, step 102 may further comprise a first mating member of the diagnostic analyzer mating with a second mating member of the shaft to cause the shaft to rotate as it moves between positions. In one embodiment, the first and second mating members comprise a pin and a groove mating. In other embodiments, the first and second mating members may vary. In still another embodiment, the at least one reaction vessel moving member may vary.

In step 104, the rotating device is rotated along an optical path. In one embodiment, step 104 comprises rotating a turret along an optical path. In another embodiment, the rotating device may vary. In step 106, the first darkened compartment of the rotating device is read with a first optical reader in order to take a reading of a first sample disposed in the first reaction vessel. In step 108, the second darkened compartment of the rotating device is read with a second optical reader in order to take a reading of a second sample disposed in the second reaction vessel.

In one embodiment, steps 106 and 108 comprise a first reaction vessel holding member of the first darkened compartment holding the first reaction vessel containing the first sample, and a second reaction vessel holding member of the second darkened compartment holding the second reaction vessel containing the second sample. In one embodiment, steps 106 and 108 comprise a first ledge of the first darkened compartment holding the first reaction vessel, and a second ledge of the second darkened compartment holding the second reaction vessel. In another embodiment, steps 106 and 108 comprise a first pivoting member of the first darkened compartment holding the first reaction vessel, and a second pivoting member of the second darkened compartment holding the second reaction vessel. In other embodiments, the first and second reaction vessel holding members may vary.

In step 110, a first push-out member disposed in the first darkened compartment pushes the first reaction vessel away from the first reaction vessel holding member and out of the first darkened compartment, and a second push-out member disposed in the second darkened compartment pushes the second reaction vessel away from the second reaction vessel holding member and out of the second darkened compartment.

In other embodiments, one or more steps of the method 100 may vary in substance or in order, one or more steps of the method 100 may not be followed, or one or more additional steps may be added to the method 100.

One or more embodiments of the disclosure provides a diagnostic analyzer and method of its use which uses less-costly, less space-consuming, less complex, and lower-maintenance devices, than one or more current diagnostic analyzers, to transfer reaction vessels into detection systems in order to detect conditions of samples held within the reaction vessels. One or more embodiments of the disclosure may further reduce one or more additional issues associated with one or more of the other current diagnostic analyzers and methods of their use.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. Furthermore, it is to be understood that the disclosure is defined by the appended claims. Accordingly, the disclosure is not to be restricted except in light of the appended claims and their equivalents.

The invention claimed is:

1. A diagnostic analyzer comprising:
a darkened optical reading area;
a processing track disposed proximate the darkened optical reading area, the processing track comprising a plurality of slots; and
a reaction vessel moving member configured to move a reaction vessel disposed in one of the plurality of slots out of the slot and into the darkened optical reading area.

2. The diagnostic analyzer of claim 1 wherein the reaction vessel moving member comprises a shaft.

3. The diagnostic analyzer of claim 2 wherein the shaft has a hollow interior which is sized to allow a bottom portion of the reaction vessel to be disposed within the hollow interior, and the shaft further comprises an anti-rotation member to prevent the reaction vessel from rotating relative to the shaft.

4. The diagnostic analyzer of claim 3 wherein the anti-rotation member comprises a pocket.

5. The diagnostic analyzer of claim 2 further comprising a first mating member, the shaft further comprising a second mating member, wherein the first mating member and the second mating member are mated causing the shaft to rotate as it moves between positions.

6. The diagnostic analyzer of claim 5 wherein the first mating member comprises a pin and the second mating member comprises a groove.

7. The diagnostic analyzer of claim 1 wherein the darkened optical reading area comprises a rotating device having a first darkened compartment and a second darkened compartment, the rotating device comprising an optical path along which the first darkened compartment and the second darkened compartment travel.

8. The diagnostic analyzer of claim 7 further comprising a first optical reader and a second optical reader, wherein the first optical reader is operable to read the first darkened compartment and the second optical reader is operable to read the second darkened compartment.

9. The diagnostic analyzer of claim 7 wherein the rotating device comprises a rotating turret.

10. The diagnostic analyzer of claim 7 wherein the first darkened compartment comprises a first reaction vessel holding member for holding a first reaction vessel, and the second darkened compartment comprises a second reaction vessel holding member for holding a second reaction vessel.

11. The diagnostic analyzer of claim 10 wherein the first reaction vessel holding member comprises a first ledge, and the second reaction vessel holding member comprises a second ledge.

12. The diagnostic analyzer of claim 10 wherein the first reaction vessel holding member comprises a first pivoting member, and the second reaction vessel holding member comprises a second pivoting member.

13. The diagnostic analyzer of claim 10 further comprising a first push-out member disposed in the first darkened compartment to push the first reaction vessel away from the first reaction vessel holding member and out of the first darkened compartment, and a second push-out member disposed in the second darkened compartment to push the second reaction vessel away from the second reaction vessel holding member and out of the second darkened compartment.

14. The diagnostic analyzer of claim 1 wherein the darkened optical reading area comprises a darkened compartment, a push-out member disposed within the darkened compartment, the push-out member configured to push the reaction vessel out of the darkened compartment.

15. The diagnostic analyzer of claim 1 further comprising first and second mating members which are mated together, the reaction vessel moving member comprising the second mating member, the first and second mating members configured to cause the reaction vessel moving member to rotate as it moves the reaction vessel out of the slot into the darkened optical reading area.

16. The diagnostic analyzer of claim 15 wherein the first mating member comprises a fixed pin and the second mating member comprises a groove.

17. The diagnostic analyzer of claim 1 wherein the darkened optical reading area comprises a darkened compartment, a pivoting member disposed in the darkened compartment, the pivoting member configured to rotate relative to the darkened compartment to hold the reaction vessel within the darkened compartment.

18. The diagnostic analyzer of claim 1 wherein the reaction vessel moving member has a hollow interior which is sized to hold a portion of the reaction vessel within the hollow interior.

19. The diagnostic analyzer of claim 18 wherein the reaction vessel moving member comprises an anti-rotation member configured to prevent the reaction vessel from rotating relative to the reaction vessel moving member.

20. The diagnostic analyzer of claim 1 further comprising a first optical reader and a second optical reader, wherein the darkened optical reading area comprises a first darkened compartment and a second darkened compartment, the first optical reader configured to read within the first darkened compartment simultaneously as the second optical reader reads within the second darkened compartment.

\* \* \* \* \*